US011207473B2

(12) United States Patent
Choi et al.

(10) Patent No.: US 11,207,473 B2
(45) Date of Patent: Dec. 28, 2021

(54) PORTABLE APPARATUS FOR MONITORING PATIENT COMPLIANCE

(71) Applicant: West Pharmaceutical Services, Inc., Exton, PA (US)

(72) Inventors: Jason Choi, Gilbert, AZ (US); Anthony G. Esposito, Fountain Hills, AZ (US); Paul Benson, Tyler, TX (US)

(73) Assignee: West Pharmaceutical Services, Inc., Exton, PA (US)

( * ) Notice: Subject to any disclaimer, the term of this patent is extended or adjusted under 35 U.S.C. 154(b) by 162 days.

(21) Appl. No.: 16/477,382

(22) PCT Filed: Jan. 12, 2018

(86) PCT No.: PCT/US2018/013559
§ 371 (c)(1),
(2) Date: Jul. 11, 2019

(87) PCT Pub. No.: WO2018/132701
PCT Pub. Date: Jul. 19, 2018

(65) Prior Publication Data
US 2020/0001023 A1 Jan. 2, 2020

Related U.S. Application Data

(60) Provisional application No. 62/445,914, filed on Jan. 13, 2017.

(51) Int. Cl.
*A61M 5/50* (2006.01)
*A61B 5/00* (2006.01)
*A61M 5/32* (2006.01)

(52) U.S. Cl.
CPC ......... *A61M 5/5086* (2013.01); *A61B 5/4833* (2013.01); *A61M 5/3243* (2013.01);
(Continued)

(58) Field of Classification Search
CPC ........ A61B 5/4833; A61M 2205/3327; A61M 2205/3569; A61M 2205/3584;
(Continued)

(56) References Cited

U.S. PATENT DOCUMENTS

2015/0209114 A1  7/2015  Burkholz et al.
2018/0161117 A1* 6/2018  Gylleby ................. A61B 50/24
2018/0161515 A1* 6/2018  Sanders ........... A61B 5/150274

FOREIGN PATENT DOCUMENTS

CN      101318037 A   12/2008
EP         3103493 A1  12/2016
WO     2013070705 A1   5/2013

OTHER PUBLICATIONS

Int'l Search Report and Written Opinion dated Apr. 4, 2018 in Int'l Application No. PCT/US2018/013559.
(Continued)

*Primary Examiner* — Jason E Flick
(74) *Attorney, Agent, or Firm* — BakerHostetler (57) ABSTRACT

A compliance monitoring system is provided for an injection device having an unused state and a used state. The system includes one or more radio frequency tags attached to a surface of the injection device and a portable monitoring accessory that includes a housing, a radio frequency antenna disposed within the housing, a wireless transmitter module disposed within the housing, and a processing circuit disposed within the housing. The processing circuit is configured to receive, via the radio frequency antenna, a first signal from the one or more radio frequency tags via a radio frequency communication protocol. The processing circuit is also configured to transmit, via the wireless transmitter, a second signal to a mobile device via a wireless communication protocol different from the radio frequency commu-
(Continued)

nication protocol. Both of the first signal and the second signal include state information of the injection device.

13 Claims, 4 Drawing Sheets

(52) U.S. Cl.
CPC ............... *A61M 2205/3569* (2013.01); *A61M 2205/3584* (2013.01); *A61M 2205/50* (2013.01); *A61M 2205/60* (2013.01)

(58) Field of Classification Search
CPC ...... A61M 2205/3592; A61M 2205/50; A61M 2205/60; A61M 2205/6009; A61M 5/20; A61M 5/2033; A61M 5/3243; A61M 5/5086; A61M 5/50; A61M 2205/33; A61M 2205/35; A61M 2205/3546; A61M 2205/3576; A61M 5/178; A61M 2005/2006; A61M 5/3205; A61M 5/321
See application file for complete search history.

(56) References Cited

OTHER PUBLICATIONS

Office Action dated Mar. 11, 2021 in Chinese Application No. 201880018116.4.

* cited by examiner

PORTABLE APPARATUS FOR MONITORING PATIENT COMPLIANCE

This application is a section 371 of International Application No. PCT/US18/013559, filed Jan. 12, 2018, which was published on Jul. 19, 2018 under International Publication No. WO 2018/132701 A1, which claims the benefit of U.S. Provisional Application No. 62/445,914, filed Jan. 13, 2017, the disclosures of all of which are incorporated herein by reference.

FIELD OF THE INVENTION

Embodiments of the present disclosure relate to apparatuses and techniques for communicating state information of an injection device using a reusable and portable monitoring accessory.

BACKGROUND OF THE INVENTION

Manual and auto-injection devices (or self-injectors) are medical devices designed to deliver a dose of a particular medicament into a body of a patient. Manual injection devices usually include a syringe contained within a housing wherein a needle of the syringe must be manually inserted into the skin of the patient and the plunger must also be actuated manually to deliver the medicament. Auto-injection devices are similar but are typically equipped with spring-loaded activators for needle insertion and/or medicament delivery. Both manual-type and auto-injectors are intended for self-administration of the dose by patients or other untrained personnel. These types of medical devices have at least two states, one being an unused state before the device is injected, and the other state being a used state after the device is injected.

In certain circumstances, the medical devices are identified by labels to provide users with identification and instructions for administering the medicament. However, information presented on the labels generally does not change in order to reflect a real-time status of the medical device, e.g., a use of the medical device.

Currently-available monitoring solutions for medical devices lack an ability to immediately transmit the state information of the medical devices to a mobile device in a cost effective manner. The state information of the medical device therefore cannot be used to effectively monitor and enforce patient compliance or provide prompt advice by a medical professional. In addition, administration applications may not be sufficiently supported because the state information of the medical device is not immediately available to such applications.

Part of the issue is the difficulty in designing a cost effective communication mechanism for collecting and transmitting information regarding a disposable medical device. Some approaches utilize cheap tags or chips to fulfill the task, but, need special receivers to receive the information outputted therefrom. Some approaches are capable of sending signals that can be retrieved by common receivers, but, the necessary components are generally too expensive or otherwise unsuitable for a one-time usage.

In view of the foregoing reasons, it is desirable to have a monitoring system that can collect and transmit state information of injection device in a cost effective manner.

BRIEF SUMMARY OF THE DISCLOSURE

An embodiment of the present invention comprises a compliance monitoring system for an injection device having at least an unused state and a used state. The system includes one or more radio frequency tags attached to a surface of the injection device and a portable monitoring accessory. The portable monitoring accessory includes a housing, a radio frequency antenna disposed within the housing, a wireless transmitter module disposed within the housing and a processing circuit disposed within the housing. The processing circuit is configured to receive, via the radio frequency antenna, a first signal (including state information of the injection device) from the one or more radio frequency tags via a radio frequency communication protocol, and transmit, via the wireless transmitter, a second signal (including the state information) to a mobile device via a wireless communication protocol different from the radio frequency communication protocol.

In further detail of the compliance monitoring system, the radio frequency communication protocol is an NFC protocol or an RFID protocol, and the wireless communication protocol is a Bluetooth communication protocol or a GSM communication protocol.

In still further detail of the compliance monitoring system, the state information includes a unique identifier of the injection device or a medicament contained therein, and a confirmation that the injection device is in the used state. The one or more tags are configured to collect the state information from the injection device. The state information of the injection device includes at least an injection date and time, a unique identifier of the injection device, and identification of a medicament contained in the injection device.

A compliance monitoring system is also disclosed herein. The compliance monitoring system includes an injection device containing a medicament and including a needle for delivering the medicament into a body of a patient. The injection device has at least an unused state and a used state. The compliance monitoring system also includes one or more radio frequency tags attached to a surface of the injection device and a portable monitoring accessory disposed in a vicinity of the one or more tags. The portable monitoring accessory includes a housing, a radio frequency antenna disposed within the housing, a wireless transmitter module disposed within the housing, and a processing circuit disposed within the housing. The processing circuit is configured to receive, via the radio frequency antenna, a first signal (including state information of the injection device) from the one or more radio frequency tags via a radio frequency communication protocol, and transmit, via the wireless transmitter, a second signal (including the state information) to a mobile device via a wireless communication protocol different from the radio frequency communication protocol.

In further detail of the compliance monitoring system, the injection device further includes a needle shield configured to automatically cover the needle following an injection to place the injection device in the used state.

In still further detail of the compliance monitoring system, the radio frequency communication protocol is an NFC protocol or an RFID protocol, and the wireless communication protocol is a Bluetooth communication protocol or a GSM communication protocol. The state information includes a unique identifier of the injection device or a medicament contained therein, and a confirmation that the injection device is in the used state. The one or more tags are configured to collect the state information from the injection device. The state information of the injection device includes at least an injection date and time, a unique identifier of the injection device, and identification of a medicament contained in the injection device.

A portable monitoring accessory is also disclosed herein for use in a compliance monitoring system for an injection device having at least an unused state and a used state. The accessory includes one or more radio frequency tags attached to a surface of the injection device and a housing. A radio frequency antenna, a wireless transmitter module and a processing circuit are disposed within the housing. The processing circuit is configured to receive, via the radio frequency antenna, a first signal (including state information of the injection device) from one or more radio frequency tags disposed on the injection device via a radio frequency communication protocol, and transmit, via the wireless transmitter, a second signal (including the state information) to a mobile device via a wireless communication protocol different from the radio frequency communication protocol.

In further detail of the portable monitoring accessory, the radio frequency communication protocol is an NFC protocol or an RFID protocol, and the wireless communication protocol is a Bluetooth communication protocol or a GSM communication protocol.

In still further detail of the portable monitoring accessory, the state information includes a unique identifier of the injection device or a medicament contained therein, and a confirmation that the injection device is in the used state. The state information of the injection device includes at least an injection date and time, a unique identifier of the injection device, and identification of a medicament contained in the injection device.

BRIEF DESCRIPTION OF ACCOMPANYING DRAWINGS

The foregoing summary, as well as the following detailed description of preferred embodiments of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

It should be noted that the figures are not necessarily drawn to scale and that elements of familiar structures or functions are generally represented by like reference numerals for illustrative purpose throughout the figures.

DETAILED DESCRIPTION OF ASPECTS OF THE DISCLOSURE

Certain terminology is used in the following description for convenience only and is not limiting. The words "right," "left," "lower" and "upper" designate directions in the drawings to which the reference is made. The words "inwardly" and "outwardly" refer to directions toward and away from, respectively, the geometric center of the apparatus and designated parts thereof. The terminology includes the words above specifically mentioned, derivatives thereof and words of similar import.

Figure 1:
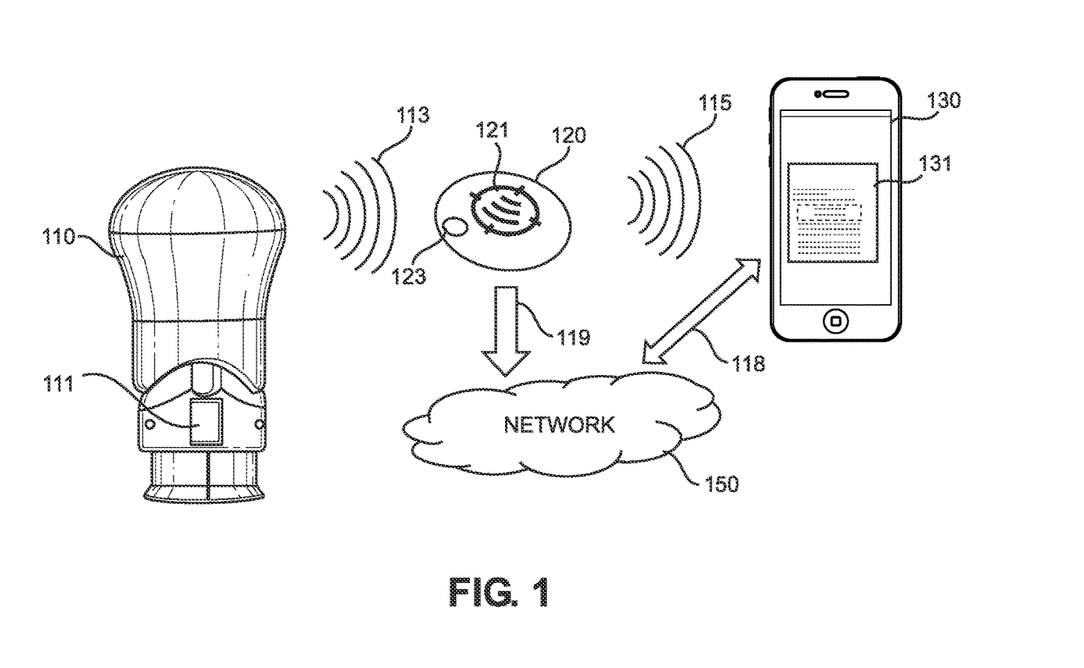
FIG. 1 is a schematic diagram of a system including a radio frequency tag on a medical device, a monitoring accessory and a mobile device for monitoring patient compliance according to an aspect of this disclosure.

FIG. 1 shows an exemplary system 100 for monitoring compliance of a patient who uses an injection device 110. Turning to FIG. 1, the system 100 may include the injection device 110, a monitoring accessory 120 and a mobile device 130.

The injection device 110 may be a self-administering device, for example, a SelfDose® device by West Pharma, which is a needle-based injection device that includes a needle coupled with an injector container for holding a medicament (collectively not shown). The injection device 110 may have at least two states reflecting a use of the injection device 110, including an unused state when the medicament of the injection device 110 has not been delivered into patient's body and a used state when the medicament has been injected.

One or more radio frequency tags 111 may be attached to a surface of the injection device 110. The radio frequency tags 111 may be made of a flexible material for tightly adhering onto a curved or other irregularly-shaped surface of the injection device 110. Each of the radio frequency tags 111 may be a radio frequency identification ("RFID") tag, a near-field communication ("NFC") tag, or the like. Alternatively, any other suitable radio frequency tags that can collect and transmit information may be attached to the injection device 110. In some embodiments, the radio frequency tags 111 may be placed internally to the injection device 110 to reduce the likelihood of tampering or accidental damage.

At least one of the radio frequency tags 111 may be configured to store an identification of the injection device 110 and/or an identification of the medicament held in the container of the injection device 110. Additionally, at least one of the radio frequency tags 111 may store collected delivery state information of the injection device 110, which state information may be collected, for example, by certain sensors (not shown) associated with the injection device 110. In some embodiments, the state information may include date, time, unique identifier of the injection device 110, the identification of the medicament injected into a body of a patient, the temperature of the medicament, and the like.

The radio frequency tags 111 may be configured to transmit the state information stored therein by a first electromagnetic waves 113 in a selected radio frequency or radio wavelength, which is suitable for short distance (or near-field) signal transfer. In case one radio frequency tag 111 is used, the radio frequency tag 111 may transmit a radio frequency signal containing a unique identifier of the medicament and/or the injection device. Additionally, the radio frequency tag 111 may transmit a confirmation of the use of the injection device 110. For example, the radio frequency tag 111 may initially be shielded (not shown) and activation of the injection device 110 can remove the shielding or otherwise expose the tag 111 to be read. Other methods may be used to enable the tag 111 to represent the state of the device 110 as well, such as sensors (not shown) in communication with the tag 111, simple circuitry (not shown) to actuate or expose the tag 111, or the like. In case of two or more tags 111 are used, at least one of the radio frequency tags 111 may transmit the unique identifier and/or the confirmation of the use of the injection device 110.

The monitoring accessory 120 may be a portable monitoring accessory and may include a receiver 121 that may be configured to receive the first electromagnetic waves 113. The receiver 121 may be a reader antenna that is configured to be closely placed to the radio frequency tags 111 for receiving near-field radio frequency signals, e.g., the injection device 110 may be brought into near-contact with the monitoring accessory 120 in order to transmit the signal. The monitoring accessory 120 may be reusable for receiving and transmitting information multiple times.

The monitoring accessory 120 may process the received signal, e.g., demodulating the signal to restore the state information of the injection device 110 and modulating the state information 110 to generate a second signal that is suitable for being transmitted via a second communication protocol that may be different from the first communication protocol. For example, the second communication protocol may be a Bluetooth communication protocol or other mobile communication protocol.

The monitoring accessory 120 may transmit the second signal in a form of a second electromagnetic wave 115 that is different than the first electromagnetic wave 113 and that is suitable for the mobile device 130 to receive. In some embodiments, the second electromagnetic wave 115 may be transferred to a mobile device 130 over a distance farther than the distance between the injection device 110 and the monitoring accessory 120.

The mobile device 130 may be a personal computing device, including, but not limited to a smartphone, tablet, laptop, and other personal digital assistant that can run applications, such as a medical analysis application that operates upon the received state information of the injection device 110. According to some aspects of the disclosure, the mobile device 130 may run an application to receive, process, analyze, display and/or transmit the received information to a server and/or database (not shown) connected to a network 150, via channel 118, which may be any type of wired or wireless connection and corresponding protocol. A medical professional may access the server and/or database for analyzing collected state information, monitoring a patient's compliance with a dosage regimen, and/or providing professional advice. The state information, results of the analysis and/or the professional advices may be accessible by the patient or other authorized personals via the mobile device 130 or any other suitable devices. In order to comply with privacy regulations, access to the information is preferably restricted, as is conventionally known.

Additionally and/or alternatively, the monitoring accessory 120 may be configured to directly transmit the state information of the injection device 110 to a server or computer connected to the network 150, at channel 119 (e.g., over Wi-Fi, GSM, or other similar type of wireless or wired connection), when an access point to the network 150 is available. The state information and the analysis result may be made accessible by the patient via the mobile device 130 or any other suitable devices.

Figure 2:
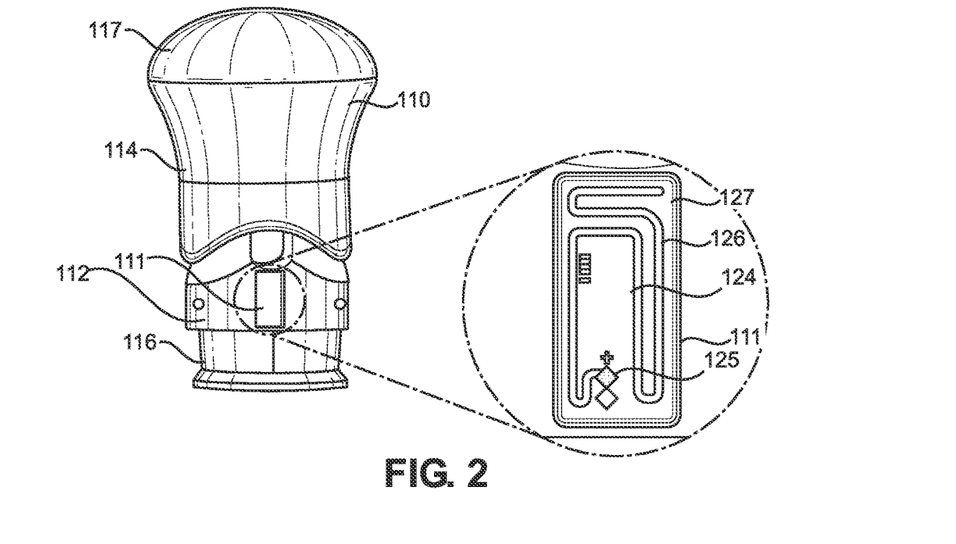
FIG. 2 is an enlarged side elevational view of the radio frequency tag used in the system of FIG. 1.

Referring to FIG. 2, the injection device 110 may include a syringe (not shown) for holding a medicament (not shown) for injecting into a body of a patient, a handle 114 for delivering the medicament into the body of the patient, and a needle guard 116 which preferably automatically actuates to cover the needle following injection for preventing a needle stick injury.

The radio frequency tag 111 may be an NFC or RFID tag that may be attached to a lower housing part 112 of the injection device 110. The radio frequency tag 111 may include, but not is limited to, an integrated circuit 125 and an antenna 126, which may transmit electromagnetic waves in a vicinity of the radio frequency tag 111. In some embodiments, the radio frequency tag 111 may apply Automatic Identification and Data Capture ("AIDC") technologies to automatically identify the injection device 110 and/or collect state information of the injection device 110.

Although shown and described as being attached to the lower housing part 112 of the injection device 110 for purposes of illustration only, the radio frequency tag 111 may be attached to any suitable surface of the injection device 110, e.g., a top surface 117 of the injection device 110.

The radio frequency tag 111 may be a passive radio frequency tag or an active radio frequency tag depending on whether the radio frequency tag 111 is provided with a power source. A passive radio frequency tag may be provided with no power source and, therefore, may be powered by energy received by the antenna 126 in the form of an external radio frequency interrogation signal (sent, for example, by the monitoring accessory 120). An active radio frequency tag may be provided with a power source, e.g., a battery, and able to transmit the state information to a receiver on its own, i.e., without absorbing power from the receiver. Usually, an active radio frequency tag may be read from a distance farther than a passive radio frequency tag.

The integrated circuit 125 and the antenna 126 may be attached to a substrate 127 that may be a Mylar or plastic film. The substrate 127 may be flexible and/or stretchable for tightly attaching to a curved surface of the injection device 110.

Although shown and described as including an integrated circuit (or chip) 125 and an antenna 126 for purposes of illustration only, the radio frequency tag 111 may include other elements, e.g., various sensors, microprocessors, input and/or output ports, and/or the like.

Figure 3:
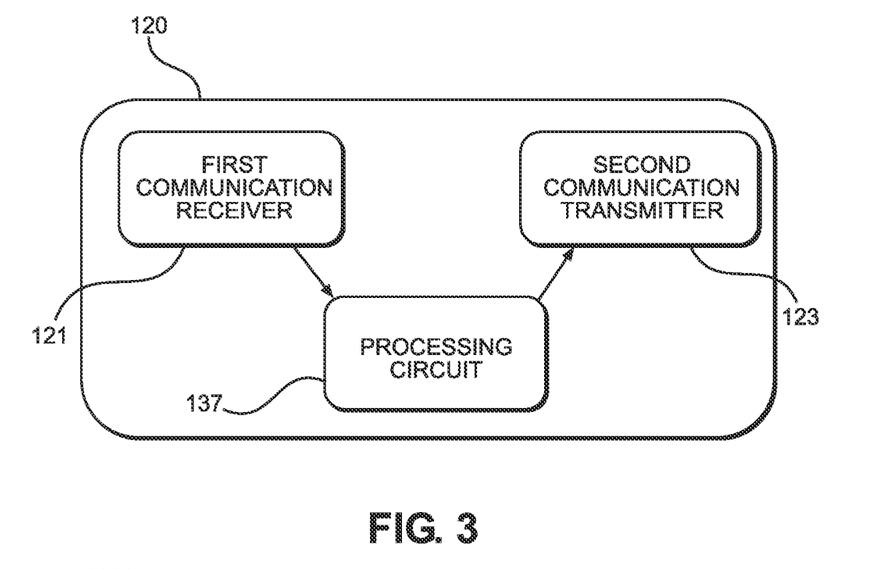
FIG. 3 is a schematic diagram of the monitoring accessory included in the system of FIG. 1.

FIG. 3 is a schematic diagram of the monitoring accessory 120 in accordance with an embodiment of the present invention. The monitoring accessory 120 may include a first communication protocol receiver 121, a second communication protocol transmitter 123, both of which are preferably coupled to a processing circuit 137.

The first communication receiver 121 may be provided to receive a first modulated signal in a radio frequency, which first modulated signal may include as data a state information of the injection device 110 of FIG. 2. The radio frequency signal may be transmitted from the radio frequency tag 111 of FIG. 2. The first communication receiver 121 may be an antenna configured to receive a radio frequency signal.

The received radio frequency signal may be demodulated by the processing circuit 137 to retrieve the state information of the injection device 110. The processing circuit 137 may include, but is not limited to, printed circuits, various electrical elements, memories, and/or a processor. The processing circuit 137 may be configured to thereafter modulate the state information based on a second communication protocol that may be a wireless communication protocol, e.g., a Bluetooth communication protocol, a WiFi communication protocol or a suitable mobile communication protocol.

The modulated state information may be transmitted via the second communication transmitter 123. The second communication transmitter 123 may include a Bluetooth communication module, a WiFi communication module and/or a mobile communication module for communicating with a mobile device, a WiFi network and a mobile network, respectively.

Although shown and described as Bluetooth, WiFi and mobile communication modules for purposes of illustration only, other suitable wireless communication approaches may be used for transmitting the state information to the mobile device or a network.

Figures 4A, 4B:
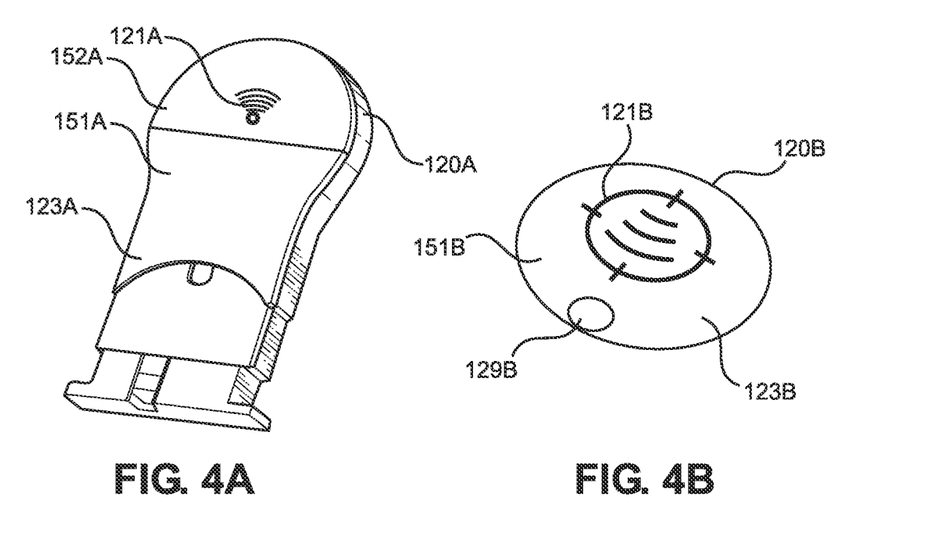
FIGS. 4A and 4B are perspective views of a first type and a second type, respectively, of the monitoring accessory included in the system of FIG. 1.

FIGS. 4A and 4B show two sample embodiments of the monitoring accessory 120. Referring to FIG. 4A, a handheld-type monitoring accessory 120A may be used to scan the radio frequency tag 111 attached to the injection device 110 and transmit the scanned information to a mobile device 130 or a network 150 (collectively shown in FIG. 1).

The handheld-type monitoring accessory 120A may include a radio frequency receiver (or antenna) 121A disposed within a mushroom-shaped housing 151A for receiving a radio frequency signal in a first communication protocol. The receiver 121A may be positioned in a head portion 152A of the mushroom-shaped monitoring accessory 120A for easy operation while holding a handle portion of the housing 151A of the monitoring accessory 120A. According to aspects of this disclosure, the radio frequency receiver 121A may be enclosed in any suitable position of the mushroom-shaped monitoring accessory 120A. While in this embodiment, the accessory 120A is shown as having a mushroom shape, the shape is not limiting and other shapes can work as well.

A second communication transmitter 123A may be disposed in a suitable position within the body portion 151A for transmitting scanned information in a second communication protocol. Operation of the second communication transmitter 123A may be signaled to the user by a visual and/or audible indicator (not shown).

Referring to FIG. 4B, a desktop monitoring-type accessory 120B may be provided for scanning the state information of the injection device 110 and transmitting the state information to the mobile device 130 or the network 150.

The desktop monitoring accessory 120B may include a radio frequency receiver 121B disposed within a button-shaped housing 151B for receiving a radio frequency signal in a first communication protocol. The radio frequency receiver 121B may be positioned beneath an upper surface of the monitoring accessory 120B for easy scanning while holding the injection device 110 in the palm of the hand, or while the monitoring 120B accessory is supported on a surface, such a desk, table-top, or the like. In some embodiments, the radio frequency receiver 120B may be positioned in any suitable portion of the button-shaped monitoring accessory 120B.

A second communication transmitter 123B may be disposed in any position within the housing 151B for transmitting the state information in a second communication protocol. Operation of the second communication transmitter 123B may be signaled to the user by a visual and/or audible indicator 129B.

Figure 5:
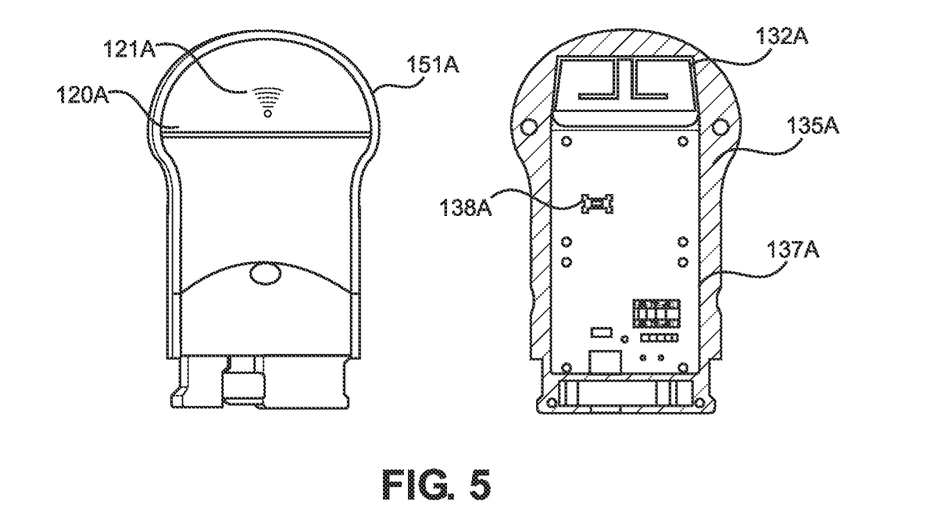
FIG. 5 is a front side elevational and cross-sectional view of the first type of the monitoring accessory of FIG. 3.

FIG. 5 is a cross-sectional view of the mushroom-shaped monitoring accessory 120A in FIG. 4A. Referring to FIG. 5, the mushroom-shaped monitoring accessory 120A may include a circuit housing 135A, a radio frequency antenna 132A and a printed circuit board 137A. The printed circuit board 137A may include various electronic components, including, but not limited to, a transmitter module 138A and a microprocessor (not shown). A cover 151A may be provided in a similar shape of the circuit housing 135A for protecting electrical components enclosed therein, including the radio frequency antenna 132A, the printed circuit board 137A, the transmitter module 138A and the like.

The radio frequency antenna 132A may be attached to the circuit housing 135A and configured to receive radio frequency signals from the radio frequency tag 111 (shown in FIG. 1). The radio frequency antenna 132A may be an inlay type and made in a suitable shape to receive the radio frequency signals. The radio frequency antenna 132A may be disposed in a top part of the monitoring accessory 120A or in any other suitable parts of the monitoring accessory 120A.

The printed circuit board 137A may be attached to the circuit housing 135A and may include the transmitter module 138A and other electronic components, including, but not limited to, a visual indicator, an audio indicator, a power source and the like (collectively not shown in FIG. 5). The power source may include a battery and/or a hardwired power source for providing electrical power to the electronic components of the monitoring accessory 110A, such as, the radio frequency antenna 132A and the printed circuit board 137A. The visual indicator and/or the audio indicator may be configured to indicate an operation status of the monitoring accessory 110A, e.g., the visual indicator may illuminate when the power source is turned on, and the audible indicator may beep when a radio frequency signal is received by the monitoring accessory 110A and/or a second signal is transmitted.

The microprocessor may be configured to process the received radio frequency signal, including, but not limited to, demodulating the radio frequency signal to retrieve the state information of the injection device 110 and modulating the state information according to a second communication protocol, e.g., a Bluetooth communication protocol, a WiFi communication protocol or a mobile communication protocol, for transmitting the state information to a mobile device 130 or a network 150 (collectively shown in FIG. 1).

The transmitter module 138A may be a Bluetooth module or a GSM module and imbedded in or plugged onto the printed circuit board 137A. The transmitter module 138A may be configured to transmit the modulated state information, via the second communication protocol.

Although shown and described as modulating and transmitting the state information in the Bluetooth communication protocol, the WiFi communication protocol or the GSM communication protocol for purposes of illustration only, any other suitable wireless communication protocols may be utilized to transmit the state information to a server or to other wireless devices or facilities associated with the network 150. For example, CDMA, LTE and/or future 5G mobile communication protocols may be used to transmit the state information to the network 150.

Figure 6:
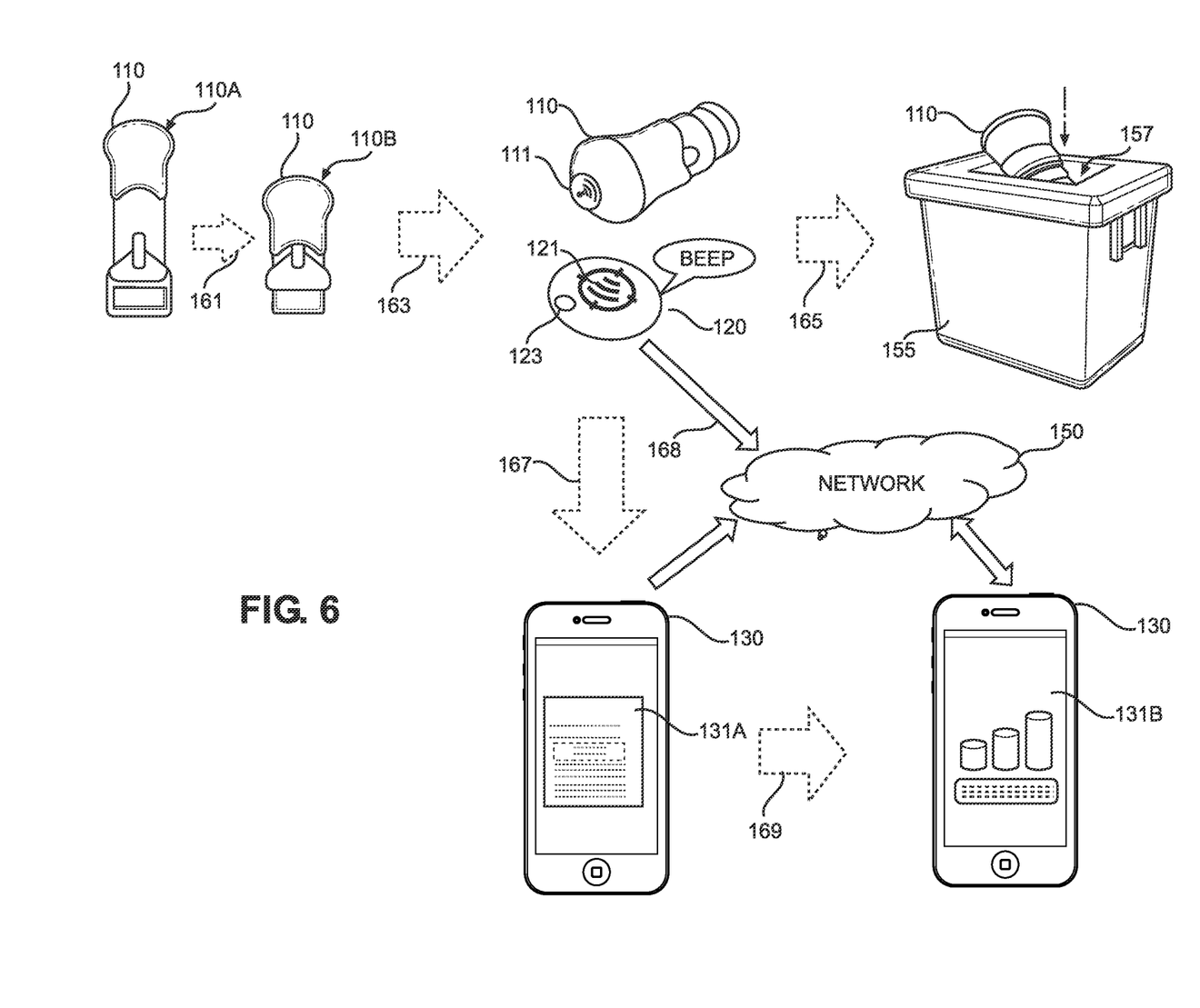
FIG. 6 is a schematic diagram of a process for using the system for monitoring compliance of FIG. 1.

FIG. 6 is a flow diagram showing a monitoring process for an injection device 110 using the monitoring accessory 120. Referring to FIG. 6, the injection device 110 may include at least two states, namely, an unused state 110A and a used state 110B.

When the injection device 110 has delivered a medicament contained therein into a body of a patient, the injection device 110 changes its state from the unused state 110A to the used state 110B, at 161. A sensor may detect the state change and pass it to at least one radio frequency tag 111 attached to the injection device 110B that may record the state change as a result of the delivery. As shown and described above, recorded state information of the injection device 110B may include a date and time of the delivery, a unique identifier of the injection device 110 and/or an identification of the medicament delivered and the like. The state information of the injection device 110B may be collected and recorded by the radio frequency tag 111 (shown in FIG. 1) of the injection device 110. The radio frequency tag 111 may modulate the state information with a first communication protocol for transmitting the state information to a vicinity of the injection device 110. The first communication protocol may be a radio frequency communication protocol.

At step 163, the radio frequency tag 111 may be scanned or read by the monitoring accessory 120 for receiving the modulated state information of the injection device 110 therefrom. The modulated state information received from the radio frequency tag 111 may be demodulated by a processor (not shown) to retrieve the state information. The state information may be modulated in a second communication protocol and transferred to a nearby mobile device or facility.

The injection device 110 may thereafter be disposed into an opening 157 of a sharps bin 155, at step 165, for preventing sharp needle injuries after being scanned by the desktop monitoring accessory 120.

The state information modulated with the second communication protocol may be received by the mobile device 130, at step 167, or alternatively by the wireless network 150, at step 168. If the modulated state information is received by the mobile device 130, for example, an application running on the mobile device 130 may be configured to demodulate the received state information with or without user intervention. In some embodiments, a user may login onto the application via a screen 131A to upload the state information to a server and/or store the state information in a database.

At step 169, the mobile device 130 of the patient or some other entity may access the uploaded state information from the server. A medical professional may display and/or analyze the uploaded state information by the same application tool or a different application tool via a display 131B. The medical professional may monitor and/or enforce a medical adherence of the patient via providing instructions, comments, alerts and/or reminders to the patient. Alternatively and/or additionally, the patient may access the state information of the injection device 110 via the display 131B for purposes of verifying the uploaded state information and/or learning the instructions, comments, alerts and/or reminders from the medical professional.

Although shown and described as using the same mobile device 130 for accessing the state information from the server for purposes of illustration only, the uploaded state information may be accessed or used for any authorized purposes, by any authorized persons and via any suitable devices.

Various aspects of the disclosure have been presented above. However, the invention is not intended to be limited to the specific aspects presented above, which have been presented for purposes of illustration. Rather, the invention extends to functional equivalents as would be within the scope of the appended claims. Those skilled in the art, having the benefit of the teachings of this specification, may make numerous modifications without departing from the scope and spirit of the invention in its various aspects.

What is claimed is:

1. A compliance monitoring system for an injection device having at least an unused state and a used state, the system comprising:
   one or more radio frequency tags attached to a surface of the injection device and configured to collect and store state information from the injection device, the state information including at least a confirmation that the injection device is in the used state; and
   a portable monitoring accessory including a housing, a radio frequency antenna disposed within the housing, a wireless transmitter module disposed within the housing, and a processing circuit disposed within the housing, the processing circuit being configured to:
   receive, via the radio frequency antenna, a first signal from the one or more radio frequency tags via a radio frequency communication protocol, the first signal including the stored state information of the injection device, and
   transmit, via the wireless transmitter module, a second signal to a mobile device via a wireless communication protocol different from the radio frequency communication protocol, the second signal including the state information.

2. The compliance monitoring system of claim 1, wherein the radio frequency communication protocol is an NFC protocol or an RFID protocol, and wherein the wireless communication protocol is a Bluetooth communication protocol or a GSM communication protocol.

3. The compliance monitoring system of claim 1, wherein the stored state information further includes a unique identifier of the injection device or a medicament contained therein.

4. The compliance monitoring system of claim 1, wherein the stored state information of the injection device further includes at least an injection date and time, a unique identifier of the injection device, and identification of a medicament contained in the injection device.

5. A compliance monitoring system comprising:
   an injection device containing a medicament and including a needle for delivering the medicament into a body of a patient, the injection device having at least an unused state and a used state;
   one or more radio frequency tags attached to a surface of the injection device and configured to collect and store state information from the injection device, the state information including at least a confirmation that the injection device is in the used state; and
   a portable monitoring accessory disposed in a vicinity of the one or more tags, the portable monitoring accessory including a housing, a radio frequency antenna disposed within the housing, a wireless transmitter module disposed within the housing, and a processing circuit disposed within the housing, the processing circuit being configured to:
   receive, via the radio frequency antenna, a first signal from the one or more radio frequency tags via a radio frequency communication protocol, the first signal including the stored state information of the injection device, and
   transmit, via the wireless transmitter module, a second signal to a mobile device via a wireless communication protocol different from the radio frequency communication protocol, the second signal including the state information.

6. The compliance monitoring system of claim 5, wherein the injection device further includes a needle shield configured to automatically cover the needle following an injection to place the injection device in the used state.

7. The compliance monitoring system of claim 5, wherein the radio frequency communication protocol is an NFC protocol or an RFID protocol, and wherein the wireless communication protocol is a Bluetooth communication protocol or a GSM communication protocol.

8. The compliance monitoring system of claim 5, wherein the stored state information further includes a unique identifier of the injection device or a medicament contained therein.

9. The compliance monitoring system of claim 5, wherein the stored state information of the injection device further includes at least an injection date and time, a unique identifier of the injection device, and identification of a medicament contained in the injection device.

10. A portable monitoring accessory for use in a compliance monitoring system for an injection device having at least an unused state and a used state, the accessory comprising:
one or more radio frequency tags attached to a surface of the injection device; and
a housing;
a radio frequency antenna disposed within the housing;
a wireless transmitter module disposed within the housing; and
a processing circuit disposed within the housing, the processing circuit being configured to:
receive, via the radio frequency antenna, a first signal from one or more radio frequency tags disposed on the injection device via a radio frequency communication protocol, the first signal including state information of the injection device stored in the one or more radio frequency tags on the injection device, the stored state information including at least a confirmation that the injection device is in the used state, and
transmit, via the wireless transmitter module, a second signal to a mobile device via a wireless communication protocol different from the radio frequency communication protocol, the second signal including the state information.

11. The portable monitoring accessory of claim 10, wherein the radio frequency communication protocol is an NFC protocol or an RFID protocol, and wherein the wireless communication protocol is a Bluetooth communication protocol or a GSM communication protocol.

12. The portable monitoring accessory of claim 10, wherein the state information includes a unique identifier of the injection device or a medicament contained therein.

13. The portable monitoring accessory of claim 10, wherein the state information of the injection device includes at least an injection date and time, a unique identifier of the injection device, and identification of a medicament contained in the injection device.

* * * * *